United States Patent [19]

Moore

[11] 4,420,426
[45] Dec. 13, 1983

[54] 6-ALPHA-HALOPENICILLANIC ACID 1,1-DIOXIDES

[75] Inventor: Bernard S. Moore, Waterford, Conn.

[73] Assignee: Pfizer Inc., New York, N.Y.

[21] Appl. No.: 214,757

[22] Filed: Dec. 9, 1980

Related U.S. Application Data

[63] Continuation-in-part of Ser. No. 17,810, Mar. 5, 1979, abandoned.

[51] Int. Cl.$^3$ ............................................ C07D 499/00
[52] U.S. Cl. .............................. 260/245.2 R; 424/270; 424/271; 260/239.1
[58] Field of Search .................. 260/245.2 R; 424/270

[56] References Cited

U.S. PATENT DOCUMENTS

| | | | |
|---|---|---|---|
| 3,197,466 | 7/1965 | Chow et al. | 260/239.1 |
| 3,206,469 | 9/1965 | Pifferi | 260/307.7 |
| 3,741,959 | 6/1973 | Looker et al. | 260/239.1 |
| 4,203,992 | 5/1980 | Gordon et al. | 424/271 |
| 4,272,439 | 6/1981 | Ganguly et al. | 260/245.2 R |

FOREIGN PATENT DOCUMENTS

| | | |
|---|---|---|
| 866845 | 11/1978 | Belgium . |
| 881675 | 8/1980 | Belgium . |
| 13617 | 7/1980 | European Pat. Off. . |
| 2824535 | 12/1978 | Fed. Rep. of Germany . |
| 1072108 | 6/1967 | United Kingdom . |
| 2044255 | 10/1980 | United Kingdom . |

OTHER PUBLICATIONS

Cignarella et al., Journal of Organic Chemistry, 27, 2668 (1962).
Harrison et al., Journal of the Chemical Society (London), Perkin I, 1772 (1976).
Busson et al., "Recent Advances in the Chemistry of Beta-Lactam Antibiotics", J. Elks, ed., Burlington House, London, 1977, Chapter 32, pp. 304–313.
Clayton, Journal of the Chemical Society (London), Part C, 2123 (1969).
Cartwright et al., Nature, 278, 360 (1979).

Primary Examiner—Nicholas S. Rizzo
Attorney, Agent, or Firm—Connolly and Hutz

[57] ABSTRACT

A process for the preparation of penicillanic acid 1,1-dioxide and esters thereof readily hydrolyzable in vivo, which comprises oxidation of a 6-halopenicillanic acid, or an ester thereof readily hydrolyzable in vivo, to the corresponding 6-halopenicillanic acid 1,1-dioxide or ester thereof, followed by dehalogenation (e.g. by hydrogenolysis). Certain of the 6-halopenicillanic acid 1,1-dioxides and esters thereof readily hydrolyzable in vivo are novel intermediates. Penicillanic acid 1,1-dioxide, and esters thereof readily hydrolyzable in vivo are known compounds which are beta-lactamase inhibitors and which enhance the effectiveness of certain beta-lactam antibiotics (e.g. the penicillins) in the treatment of bacterial infections in mammals, particularly humans.

7 Claims, No Drawings

6-ALPHA-HALOPENICILLANIC ACID 1,1-DIOXIDES

CROSS-REFERENCE TO RELATED APPLICATIONS

This application is a continuation-in-part of application Ser. No. 017,810, filed Mar. 5, 1979 and now abandoned.

BACKGROUND OF THE INVENTION

This invention relates to a new chemical process, and to new chemical compounds useful as intermediates in said process. More particularly, it relates to a new chemical process for the preparation of penicillanic acid 1,1-dioxide and esters thereof readily hydrolyzable in vivo. Said new chemical process comprises oxidation of a 6-halopenicillanic acid, or ester thereof readily hydrolyzable in vivo, to the corresponding 1,1-dioxide, followed by dehalogenation. Said new chemical compounds useful as intermediates are 6-alpha-halopenicillanic acid 1,1-dioxides and esters thereof readily hydrolyzable in vivo.

Penicillanic acid 1,1-dioxide and esters thereof readily hydrolyzable in vivo are useful as beta-lactamase inhibitors and as agents which enhance the effectiveness of certain beta-lactam antibiotics when the latter are used to treat bacterial infections in mammals, particularly humans. Previously, penicillanic acid 1,1-dioxide and esters thereof readily hydrolyzable in vivo have been prepared from 6-alpha-bromopenicillanic acid, or ester thereof readily hydrolyzable in vivo, by debromination to give penicillanic acid, or ester thereof readily hydrolyzable in vivo, followed by oxidation to the 1,1-dioxide. Although the process of the present invention starts with a 6-halopenicillanic acid, or ester thereof readily hydrolyzable in vivo, and involves the steps of dehalogenation and oxidation, surprisingly it is found that, if the oxidation step is performed before the dehalogenation step, a better yield of product is obtained. See British patent application No. 2,000,138A, published Jan. 4, 1979; Belgian Pat. No. 867,859, granted Dec. 6, 1978; and West German Offenlegungsschrift No. 2,824,535, published Dec. 14, 1978 for details of methods of preparing penicillanic acid 1,1-dioxide and esters thereof readily hydrolyzable in vivo.

6-alpha-Halopenicillanic acids have been disclosed by Cignarella et al., *Journal of Organic Chemistry*, 27, 2668 (1962) and in U.S. Pat. No. 3,206,469; hydrogenolysis of 6-alpha-halopenicillanic acids to penicillanic acid is disclosed in British Patent Specification No. 1,072,108.

Harrison et al., *Journal of the Chemical Society* (London), Perkin I, 1772 (1976) disclose: (a) the oxidation of 6,6-dibromopenicillanic acid with 3-chloroperbenzoic acid, to give a mixture of the corresponding alpha- and beta-sulfoxides; (b) oxidation of methyl 6,6-dibromopenicillanate with 3-chloroperbenzoic acid to give a methyl 6,6-dibromopenicillanate 1,1-dioxide; (c) oxidation of methyl 6-alpha-chloropenicillanate with 3-chloroperbenzoic acid, to give a mixture of the corresponding alpha- and beta-sulfoxides; and (d) oxidation of methyl 6-alpha-bromopenicillanate with 3-chloroperbenzoic acid, to give a mixture of the corresponding alpha- and beta-sulfoxides.

Clayton, *Journal of the Chemical Society* (London), Part C, 2123 (1969) discloses inter alia: (a) 6-alpha-iodopenicillanic acid and its methyl ester; and (b) 6,6-diiodopenicillanic acid and its methyl ester.

SUMMARY OF THE INVENTION

This invention relates to a process for preparation of a compound of the formula

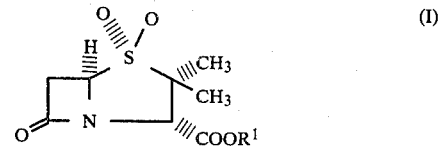

or a pharmaceutically-acceptable base salt thereof, wherein $R^1$ is selected from the group consisting of hydrogen and ester forming residues readily hydrolyzable in vivo, which comprises the steps of:

(a) contacting a compound selected from the group consisting of

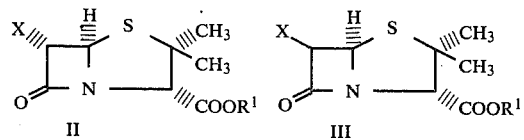

and base salts thereof with a reagent selected from the group consisting of alkali metal permanganates, alkaline earth metal permanganates and organic peroxycarboxylic acids, to give a compound selected from the group consisting of

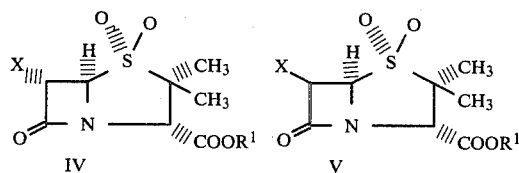

and base salts thereof, wherein X is selected from the group consisting of chloro, bromo and iodo; and (b) dehalogenating the compound of the formula IV or V, or mixture thereof.

A preferred way of carrying out step (b) comprises contacting the product of step (a) with hydrogen, in an inert solvent, at a pressure in the range from about 1 to about 100 kg/cm$^2$, at a temperature in the range from about 0° to about 60° C., and at a pH in the range from about 4 to about 9, and in the presence of a hydrogenolysis catalyst. The hydrogenolysis catalyst is usually present in an amount from about 0.01 to about 2.5 weight-percent, and preferably from about 0.1 to about 1.0 weight-percent, based on the halo-sulfone.

The preferred value for X is bromo, and the preferred reagents for carrying out step (a) are potassium permanganate and 3-chloroperbenzoic acid.

Also embraced within the ambit of this invention are the intermediates of formula IV, wherein X and $R^1$ are as defined above, and the base salts of those compounds wherein $R^1$ is hydrogen. A preferred intermediate is 6-alpha-bromopenicillanic acid 1,1-dioxide, the compound of formula IV, wherein X is bromo and $R^1$ is hydrogen, and also readily hydrolyzable esters thereof, and base salts thereof. The compound of formula IV, wherein X is bromo and $R^1$ is hydrogen, can also be called (2S,5R,6S)-6-alpha-bromo-3,3-dimethyl-7-oxo-4-thia-1-azabicyclo[3.2.0]heptane-2-carboxylic acid, S,S-dioxide.

By the term readily hydrolyzable as used herein, is meant readily hydrolyzable in vivo.

The intermediates of formula V, wherein X and $R^1$ are as defined previously, are being claimed in application Ser. No. 214,742 filed Dec. 9, 1980. The process for preparing a compound of formula I, which comprises steps (a) and (b), above, is being claimed in application Ser. No. 214,756 filed Dec. 9, 1980.

DETAILED DESCRIPTION OF THE INVENTION

This invention relates to the preparation of compounds of the formula I, and to several intermediates therefor. Throughout this specification, these compounds are named as derivatives of penicillanic acid, which is represented by the following structural formula:

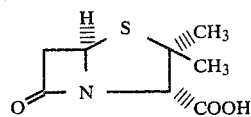

(VI)

In derivatives of penicillanic acid, broken line attachment of a substituent to the bicyclic nucleus indicates that the substituent is below the plane of the nucleus. Such a substituent is said to be in the alpha-configuration. Conversely, solid line attachment of a substituent to the bicyclic nucleus indicates that the substituent is above the plane of the nucleus. This latter configuration is referred to as the beta-configuration. Thus, the group X has the alpha-configuration in formula IV and the beta-configuration in formula V.

In this specification, when $R^1$ is an ester-forming residue readily hydrolyzable in vivo, it is a grouping which is notionally derived from an alcohol of the formula $R^1$—OH, such that the moiety $COOR^1$ in such a compound of formula I represents an ester grouping. Moreover, $R^1$ is of such a nature that the grouping $COOR^1$ is readily cleaved in vivo to liberate a free carboxy group (COOH). That is to say, $R^1$ is a group of the type that when a compound of formula I, wherein $R^1$ is an ester-forming residue readily hydrolyzed in vivo, is exposed to mammalian blood or tissue, the compound of formula I, wherein $R^1$ is hydrogen, is readily produced. The groups $R^1$ are well known in the penicillin art. In most instances, they improve the absorption characteristics of the penicillin compound. Additionally, $R^1$ should be of such a nature that it imparts pharmaceutically-acceptable properties to a compound of formula I, and it liberates pharmaceutically-acceptable fragments when cleaved in vivo. The groups $R^1$ are well known and are readily identified by those skilled in the penicillin art. See, for example, West German Offenlegungsschrift No. 2,517,316. Specific examples of groups for $R^1$ are 3-phthalidyl, 4-crotonolactonyl, gamma-butyrolacton-4-yl and groups of the formula

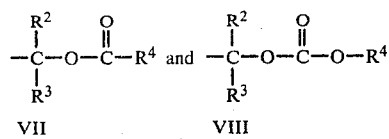

wherein $R^2$ and $R^3$ are each selected from the group consisting of hydrogen and alkyl having from 1 to 2 carbon atoms, and $R^4$ is alkyl having from 1 to 5 carbon atoms. However, preferred groups for $R^1$ are alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl.

3-Phthalidyl, 4-crotonolactonyl and gamma-butyrolacton-4-yl refer to structures IX, X and XI. The wavy lines are intended to denote either of the two epimers or a mixture thereof.

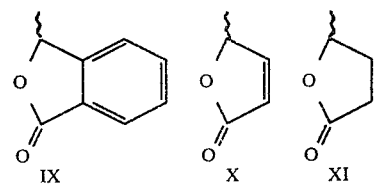

Step (a) of the process of this invention involves oxidation of the sulfide grouping in a compound of the formula II or III, or mixture thereof, to a sulfone grouping, thereby producing a compound of the formula IV or V, or mixture thereof. A wide variety of oxidants known in the art for the oxidation of sulfides to sulfones can be used for this process. However, particularly convenient reagents are alkali metal permanganates such as sodium and potassium permanganate; alkaline earth metal permanganates, such as calcium and barium permanganates; and organic peroxycarboxylic acids, such as peracetic acid and 3-chloroperbenzoic acid.

When a compound of the formula II or III, or mixture thereof wherein $R^1$ and X are as defined previously, is oxidized to the corresponding compound of the formula IV or V, or mixture thereof, using a metal permanganate, the reaction is usually carried out by treating the compound of the formula II or III or mixture thereof with from about 0.5 to about ten molar equivalents, and preferably from about one to about four molar equivalents, of the permanganate in an appropriate, reaction-inert solvent system. An appropriate, reaction-inert solvent system is one that does not adversely interact with either the starting materials or the product, and water is commonly used. If desired, a co-solvent which is miscible with water but will not interact with the permanganate, such as tetrahydrofuran, can be added. The reaction can be carried out at a temperature in the range from about −30° to about 50° C., and it is preferably carried out from about −10° to about 10° C. At about 0° C. the reaction is normally substantially complete within a short period, e.g. within one hour. Although the reaction can be carried out under neutral, basic or acid conditions, it is usual to operate at a pH in the range from about 4 to about 9, preferably 6–8. However, it is essential to choose conditions which avoid decomposition of the beta-lactam ring system of the compound of the formulae II and III. Indeed, it is often advantageous to buffer the pH of the reaction medium in the vicinity of neutrality. The sulfone is recovered by conventional techniques. Any excess permanganate is usually decomposed using sodium bisulfite, and then if the product is out of solution, it is recovered by filtration. It is separated from manganese dioxide by extracting it into an organic solvent and removing the solvent by evaporation. Alternatively, if the product is not out of solution at the end of the reaction, it is isolated by the usual procedure of solvent extraction.

When a compound of the formula II or III, or mixture thereof, wherein X and $R^1$ are as previously defined, is oxidized to the corresponding compound of the formula IV or V, or mixture thereof, using a peroxycarboxylic acid, the reaction is usually carried out by treating the compound of the formula II or III, or mixture thereof, with from about 1 to about 6 molar equivalents, and preferably about 2.2 molar equivalents of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about $-30°$ to about 50° C., and preferably from about 15° to about 30° C. At about 25° C., reaction times of about 2 to about 16 hours are commonly used. The product is normally isolated by removal of the solvent by evaporation in vacuo. The product can be purified by conventional methods, well known in the art. Alternatively, it can be used directly in step (b) without further purification.

Step (b) of the present process is a dehalogenation reaction. One convenient method of carrying out this transformation is to stir or shake a solution of a compound of the formula IV or V, or mixture thereof under an atmosphere of hydrogen, or hydrogen mixed with an inert diluent such as nitrogen or argon, in the presence of a hydrogenolysis catalyst. Suitable solvents for this hydrogenolysis reaction are those which substantially dissolve the starting compound of the formula IV or V, but which do not themselves suffer hydrogenation or hydrogenolysis. Examples of such solvents include ethers such as diethyl ether, tetrahydrofuran, dioxan, 1,2-dimethoxyethane; low molecular weight esters such as ethyl acetate and butyl acetate; tertiary amides such as N,N-dimethylformamide, N,N-dimethylacetamide and N-methylpyrrolidone; water; and mixtures thereof. Additionally, it is usual to buffer the reaction mixture so as to operate at a pH in the range from about 4 to about 9, and preferably from about 6 to 8. Borate and phosphate buffer systems are commonly used. Introduction of the hydrogen gas into the reaction medium is usually accomplished by carrying out the reaction in a sealed vessel, containing the compound of the formula IV or V, or mixture thereof, the solvent, the catalyst and the hydrogen. The pressure inside the reaction vessel can vary from about 1 to about 100 kg/cm$^2$. The preferred pressure range, when the atmosphere inside the reaction vessel is substantially pure hydrogen, is from about 2 to about 5 kg/cm$^2$. The hydrogenolysis is generally run at a temperature of from about 0° to about 60° C., and preferably from about 25° to about 50° C. Utilizing the preferred temperature and pressure values, hydrogenolysis generally takes place in a few hours, e.g., from about 2 hours to about 20 hours. The catalyst used in this hydrogenolysis reaction are the type of agents known in the art for this kind of transformation, and typical examples are the noble metals, such as nickel, palladium, platinum and rhodium. The catalyst is usually present in an amount from about 0.01 to about 2.5 weight-percent, and preferably from about 0.1 to about 1.0 weight-percent, based on the compound of formula IV or V, or mixture thereof. It is often convenient to suspend the catalyst on an inert support; a particularly convenient catalyst is palladium suspended on an inert support such as carbon.

Other methods can be used for reductive removal of the halogen atom X from a compound of formula IV or V, i.e. step (b). For example, X can be removed using a dissolving metal reducing system, such as zinc dust in acetic acid, formic acid or a phosphate buffer, according to well-known procedures. Alternatively, step (b) can be carried out using a tin hydride, for example a trialkyltin hydride such as tri-n-butyltinhydride.

As will be appreciated by one skilled in the art, when it is desired to prepare a compound of the formula I, wherein $R^1$ is hydrogen, a compound of the formula II or III, wherein $R^1$ is hydrogen can be subjected to steps (a) and (b) of the process disclosed and claimed herein. In other words, the process comprises oxidation, followed by dehalogenation, of a 6-halopenicillanic acid with a free carboxy group at the 3-position. However, in a further aspect of this invention, it is possible to operate either of steps (a) and (b) with the carboxy group at the 3-position blocked by a conventional penicillin carboxy protecting group. The protecting group can be removed after step (a) or step (b), with regeneration of the free carboxy group. In this regard, a variety of protecting groups conventionally used in the penicillin art to protect the 3-carboxy group can be employed. The identity of the protecting group is not critical. The only requirements for the protecting group are that: (i) it must be stable during the individual step (a) or step (b); and (ii) it must be removable from the particular compound of formula I, IV or V, using conditions under which the beta-lactam ring system remains substantially intact. For each of steps (a) and (b), typical examples are the tetrahydropyranyl group, trialkylsilyl groups, the benzyl group, substituted benzyl groups (e.g. 4-nitrobenzyl), the benzhydryl group, the 2,2,2-trichloroethyl group, the t-butyl group and the phenacyl group. Although all protecting groups are not operable in all situations, a particular group which can be used in a particular situation will be readily selected by one skilled in the art. See further: U.S. Pat. Nos. 3,632,850 and 3,197,466; British Pat. No. 1,041,985, Woodward et al, *Journal of the American Chemical Society*, 88, 852 (1966); Chauvette, *Journal of Organic Chemistry*, 36, 1259 (1971); Sheehan et al., *Journal of Organic Chemistry*, 29, 2006 (1964); and "Cephalosporin and Penicillins, Chemistry and Biology", edited by H. E. Flynn, Academic Press, Inc., 1972. The penicillin carboxy protecting group is removed in conventional manner, having due regard for the lability of the beta-lactam ring system.

The compound of formula I wherein $R^1$ is hydrogen is acidic and will form salts with basic agents. These salts can be prepared by standard techniques, such as contacting the acidic and basic components, usually in a stoichiometric ratio, in an aqueous, nonaqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate. Preferred salts of the compound of the formula I are the sodium, potassium and triethylamine salts.

The compounds of formula IV, wherein $R^1$ is hydrogen, are also acidic, and they will form salts with basic agents. These base salts are to be considered within the scope of this invention. Moreover, both pharmaceutically-acceptable salts (which are also termed physiologically acceptable salts) and pharmaceutically-unacceptable salts (which are also termed physiologically unacceptable salts) are included. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Base salts which are especially useful are metal salts, e.g. alkali metal or alkaline earth metal salts, and amine salts. Representative examples are lithium, sodium, potassium, calcium, barium, ammonia, n-propylamine, n-butylamine, aniline, cyclohexylamine, benzylamine, octylamine, diethylamine, morpholine, pyrrolidine, piperidine, triethylamine, N-ethylpiperidine, N-methylmorpholine and 1,5-diazabicyclo[4.3.0]non-5-ene salts. Preferred salts are sodium, potassium and triethylamine salts. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides, and also alkali metal salts of long-chain fatty acids, e.g. sodium 2-ethylhexanoate.

6-alpha-Chloropenicillanic acid and 6-alpha-bromopenicillanic acid are prepared by diazotization of 6-aminopenicillanic acid in the presence of hydrochloric acid and hydrobromic acid, respectively (*Journal of Organic Chemistry*, 27, 2668 [1962]). 6-alpha-Iodopenicillanic acid is prepared by diazotization of 6-aminopenicillanic acid in the presence of iodine, followed by hydrogenolysis (Clayton, *Journal of the Chemical Society* (C), 2123 [1969]). 6-beta-Chloropenicillanic acid, 6-beta-bromopenicillanic acid and 6-beta-iodopenicillanic acid are prepared by reduction of 6-chloro-6-iodopenicillanic acid, 6,6-dibromopenicillanic acid and 6,6-diiodopenicillanic acid, respectively, with tri-n-butyltin hydride. 6-Chloro-6-iodopenicillanic acid is prepared by diazotization of 6-aminopenicillanic acid in the presence of iodine chloride; 6,6-dibromopenicillanic acid is prepared by the method of Clayton, *Journal of the Chemical Society* (London) (C) 2123 (1969); and 6,6-diiodopenicillanic acid is prepared by diazotization of 6-aminopenicillanic acid in the presence of iodine.

6-beta-Iodopenicillanic acid also can be prepared from 6-alpha-trifluoromethylsulfonyloxypenicillanic acid by treatment with a metal iodide such as sodium iodide. 6-alpha-Trifluoromethylsulfonyloxypenicillanic acid can be obtained by diazotization of the benzhydryl or 4-methoxybenzyl ester of 6-beta-aminopenicillanic acid, followed by treatment with trifluoromethanesulfonic acid, to give benzhydryl or 4-methoxybenzyl 6-alpha-trifluoromethylsulfonyloxypenicillanate, followed in turn by removal of the ester protecting group using trifluoroacetic acid. Alternatively, 6-beta-iodopenicillanic acid can be obtained from benzhydryl or 4-methoxybenzyl 6-alpha-trifluoromethylsulfonyloxypenicillanate by reaction with a metal iodide, such as sodium iodide, followed by removal of the ester protecting group using trifluoroacetic acid. Also benzylhydryl or 4-methoxybenzyl 6-alpha-trifluoromethylsulfonyloxypenicillanate can be prepared from the 6-alpha hydroxy compound by acylation using trifluoromethanesulfonyl chloride.

The compound of formula I, wherein $R^1$ is hydrogen, and salts thereof, are active as antibacterial agents of medium potency both in vitro and in vivo, and the compounds of formula I, wherein $R^1$ is an ester-forming residue readily hydrolyzable in vivo are active as antibacterial agents of medium potency in vivo. Minimum inhibitory concentrations (MIC's) of penicillanic acid 1,1-dioxide against several microorganisms are shown in Table I.

TABLE I

| In Vitro Antibacterial Activity of Penicillanic Acid 1,1-Dioxide | |
|---|---|
| Microorganism | MIC (mcg./ml.) |
| *Staphylococcus aureus* | 100 |
| *Streptococcus faecalis* | 200 |
| *Streptococcus pyogenes* | 100 |
| *Escherichia coli* | 50 |
| *Pseudomonas aeruginosa* | 200 |
| *Klebsiella pneumoniae* | 50 |
| *Proteus mirabilis* | 100 |
| *Proteus morgani* | 100 |
| *Salmonella typhimurium* | 50 |
| *Pasteurella multocida* | 50 |
| *Serratia marcescens* | 100 |
| *Enterobacter aerogenes* | 25 |
| *Enterobacter clocae* | 100 |
| *Citrobacter freundii* | 50 |
| Providencia | 100 |
| *Staphylococcus epidermis* | 200 |
| *Pseudomonas putida* | 200 |
| *Hemophilus influenzae* | 50 |
| *Neisseria gonorrhoeae* | 0.312 |

The in vitro antibacterial activity of the compound of the formula I and its salts wherein $R^1$ is hydrogen makes them useful as industrial antimicrobials, for example in water treatment, slime control, paint preservation and wood preservation, as well as for topical application as a disinfectant. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

The in vivo activity of the compounds of formula I wherein $R^1$ is hydrogen or an ester-forming residue readily hydrolyzable in vivo, and the salts thereof, makes them suitable for the control of bacterial infections in mammals, including man, by both the oral and parenteral modes of administration. The compounds will find use in the control of infections caused by susceptible bacteria in human subjects, e.g. infections caused by strains of *Neisseria gonorrhoeae*.

When considering therapeutic use of a compound of the formula I, or a salt thereof, in a mammal, particularly man, the compound can be administered alone, or it can be mixed with pharmaceutically acceptable carriers or diluents. It can be administered orally or parenterally, i.e. intramuscularly, subcutaneously or intraperitoneally. The carrier or diluent is chosen on the basis of the intended mode of administration. For example, when considering the oral mode of administration, the compound can be used in the form of tablets, capsules, lozenges, troches, powders, syrups, elixirs, aqueous solutions and suspensions, and the like, in accordance with standard pharmaceutical practice. The proportional ratio of active ingredient to carrier will depend on the chemical nature, solubility and stability of the active ingredient, as well as the dosage contemplated. However, pharmaceutical compositions containing an antibacterial agent of the formula I will likely contain from about 20% to about 95% of active ingredient. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic.

The prescribing physician will ultimately determine the appropriate dose of a compound of formula I for a given human subject, and this can be expected to vary according to the age, weight, and response of the individual patient, as well as the nature and the severity of the patient's symptoms. The compound will normally be used orally at dosages in the range from about 10 to about 200 mg. per kilogram of body weight per day, and parenterally at dosages from about 10 to about 400 mg. per kilogram of body weight per day. These figures are illustrative only, however, and in some cases it may be necessary to use dosages outside these limits.

The compounds of the formula I, wherein $R^1$ is hydrogen or an ester-forming residue readily hydrolyzable in vivo, or a salt thereof, enhance the antibacterial effectiveness of beta-lactam antibiotics in vivo. That is, they lower the amount of the antibiotic which is needed to protect mice against an otherwise lethal inoculum of certain beta-lactamase producing bacteria. This ability makes them valuable for co-administration with beta-lactam antibiotics in the treatment of bacterial infections in mammals, particularly man. In the treatment of a bacterial infection, said compound of the formula I can be comingled with the beta-lactam antibiotic, and the two agents thereby administered simultaneously. Alternatively, said compound of the formula I can be administered as a separate agent during a course of treatment with a beta-lactam antibiotic. In some instances it is advantageous to pre-dose the subject with the compound of the formula I before initiating treatment with a beta-lactam antibiotic.

When using penicillanic acid 1,1-dioxide, a salt or an ester thereof readily hydrolyzable in vivo to enhance the effectiveness of beta-lactam antibiotic, it is administered preferably in formulation with standard pharmaceutical carriers or diluents. The methods of formulation discussed earlier for use of penicillanic acid 1,1-dioxide or an ester thereof readily hydrolyzable in vivo as a single-entity antibacterial agent can be used when co-administration with another beta-lactam antibiotic is intended. A pharmaceutical composition comprising a pharmaceutically-acceptable carrier, a beta-lactam antibiotic and penicillanic acid 1,1-dioxide or a readily hydrolyzable ester thereof will normally contain from about 5 to about 80 percent of the pharmaceutically acceptable carrier by weight.

When using penicillanic acid 1,1-dioxide or an ester thereof readily hydrolyzable in vivo in combination with another beta-lactam antibiotic, the sulfone can be administered orally or parenterally, i.e. intramuscularly, subcutaneously or intraperitoneally. Although the prescribing physician will ultimately decide the dosage to be used in a human subject, the ratio of the daily dosages of the penicillanic acid 1,1-dioxide or salt or ester thereof and the beta-lactam antibiotic will normally be in the range from about 1:3 to 3:1. Additionally, when using penicillanic acid 1,1-dioxide or salt or ester thereof readily hydrolyzable in vivo in combination with another beta-lactam antibiotic, the daily oral dosage of each component will normally be in the range from about 10 to about 200 mg. per kilogram of body weight and the daily parenteral dosage of each component will normally be about 10 to about 400 mg. per kilogram of body weight. These figures are illustrative only, however, and in some cases it may be necessary to use dosages outside these limits.

Typical beta-lactam antibiotics with which penicillanic acid 1,1-dioxide and its esters readily hydrolyzable in vivo can be co-administered are:
6-(2-phenylacetamido)penicillanic acid,
6-(D-2-amino-2-phenylacetamido)penicillanic acid,
6-(2-carboxy-2-phenylacetamido)penicillanic acid, and
7-(2-[1-tetrazolyl]acetamido)-3-(2-[5-methyl-1,3,4-thiadiazolyl]thiomethyl)-3-desacetoxymethylcephalosporanic acid.

Typical microorganisms against which the antibacterial activity of the above beta-lactam antibiotics is enhanced are:
*Staphylococcus aureus,*
*Haemophilus influenzae,*

*Klebsiella pneumoniae* and *Bacteroides fragilis.*

As will be appreciated by one skilled in the art, some beta-lactam compounds are effective when administered orally or parenterally, while others are effective only when administered by the parenteral route. When penicillanic acid 1,1-dioxide, a salt or an ester thereof readily hydrolyzable in vivo is to be used simultaneously (i.e. co-mingled) with a beta-lactam antibiotic which is effective only on parenteral administration, a combination formulation suitable for parenteral use will be required. When the penicillanic acid 1,1-dioxide or ester thereof is to be used simultaneously (co-mingled) with a beta-lactam antibiotic which is effective orally or parenterally, combinations suitable for either oral or parenteral administration can be prepared. Additionally, it is possible to administer preparations of the penicillanic acid 1,1-dioxide or salt or ester thereof orally, while at the same time administering a further beta-lactam antibiotic parenterally; and it is also possible to administer preparations of the penicillanic acid 1,1-dioxide or salt or ester thereof parenterally, while at the same time administering the further beta-lactam antibiotic orally.

Further details concerning the synthesis and use of the compounds of formula I are disclosed in West German Offenlegungsschrift No. 2,824,535 and U.S. Pat. No. 4,234,579.

The following examples are provided solely for the purpose of further illustration. Nuclear magnetic resonance spectra (NMR) were measured at 60 MHz for solutions in deuterochloroform ($CDCl_3$), hexadeuterioacetone ($CD_3COCD_3$) or deuterium oxide ($D_2O$), and peak positions are expressed in parts per million (ppm) downfield from tetramethylsilane or sodium 2,2-dimethyl-2-silapentane-5-sulfonate. The following abbreviations for peak shapes are used; s, singlet; bs, broad singlet; d, doublet; m, multiplet.

EXAMPLE I

6-alpha-Bromopenicillanic Acid 1,1-Dioxide

To a stirred mixture of 560 ml of water, 300 ml of dichloromethane and 56.0 g of 6-alpha-bromopenicillanic acid was added 4 N sodium hydroxide solution until a stable pH of 7.2 was achieved. This required 55 ml of sodium hydroxide. The mixture was stirred at pH 7.2 for 10 minutes and then it was filtered. The layers were separated and the organic phase was discarded. The aqueous phase was then poured rapidly, with stirring, into an oxidizing mixture which had been prepared as follows.

In a 3 liter flask was mixed 63.2 g of potassium permanganate, 1,000 ml of water and 48.0 g of acetic acid. This mixture was stirred for 15 minutes at 20° C. and then it was cooled to 0° C.

After the 6-alpha-bromopenicillanic acid solution had been added to the oxidizing mixture, a cooling bath at −15° C. was maintained around the reaction mixture. The internal temperature rose to 15° C. and then fell to 5° C. over a 20 minute period. At this point, 30.0 g of sodium metabisulfite was added with stirring over a 10 minute period at about 10° C. After a further 15 minutes, the mixture was filtered, and the pH of the filtrate was lowered to 1.2 by the addition of 170 ml of 6 N hydrochloric acid. The aqueous phase was extracted with chloroform, and then with ethyl acetate. Both the chloroform extracts and the ethyl acetate extracts were dried using anhydrous magnesium sulfate and then they were evaporated in vacuo. The chloroform solution afforded 10.0 g (16% yield) of the title compound. The ethyl acetate solution afforded 57 g of an oil, which was triturated under hexane. A white solid appeared. it was filtered off, giving 41.5 g (66% yield) of the title compound, mp 134° C. (dec.).

Analysis:-Calcd. for $C_8H_{10}BrNO_5S$: C, 30.78; H, 3.23; Br, 25.60; N, 4.49; S, 10.27%. Found: C, 31.05; H, 3.24; Br, 25.54; N, 4.66; S, 10.21%.

EXAMPLE 2

Oxidation of 6-alpha-chloropenicillanic acid and 6-alpha-iodopenicillanic acid with potassium permanganate, according to the procedure of Example 1, affords 6-alpha-chloropenicillanic acid 1,1-dioxide and 6-alpha-idopenicillanic acid 1,1-dioxide, respectively.

EXAMPLE 3

6-beta-Chloropenicillanic Acid 1,1-Dioxide

An oxidizing solution was prepared from 185 mg of potassium permanganate, 0.063 ml of 85% phosphoric acid and 5 ml of water. This oxidizing solution was added dropwise to a solution of 150 mg of sodium 6-beta-chloropenicillanate in 5 ml of water at 0°–5° C., until the purple color of the potassium permanganate persisted. Approximately half of the oxidizing solution was required. At this point, the potassium permanganate color was discharged by the addition of solid sodium bisulfite, and then the reaction mixture was filtered. Ethyl acetate was added to the filtrate and the pH was adjusted to 1.8. The layers were separated and the aqueous layer was further extracted with ethyl acetate. The combined ethyl acetate layers were washed with water, dried and evaporated in vacuo to give 118 mg of the title compound. The NMR spectrum (in $CD_3COCD_3$) showed absorption at 5.82 (d, 1H), 5.24 (d, 1H), 4.53 (s, 1H), 1.62 (s, 3H) and 1.50 (s, 3H) ppm.

The above product was dissolved in tetrahydrofuran and an equal volume of water was added. The pH was adjusted to 6.8 using dilute sodium hydroxide, the tetrahydrofuran was removed by evaporation in vacuo, and the residual aqueous solution was freeze dried. This afforded the sodium salt of the title compound.

EXAMPLE 4

6-beta-Bromopenicillanic Acid 1,1-Dioxide

To a solution of 255 mg of sodium 6-beta-bromopenicillanate in 5 ml of water, at 0° to 5° C., was added a solution prepared from 140 mg of potassium permanganate, 0.11 ml of 85% phosphoric acid and 5 ml of water, at 0° to 5° C. The pH was maintained between 6.0 and 6.4 during the addition. The reaction mixture was stirred at ph 6.3 for 15 minutes, and then the purple solution was covered with ethyl acetate. The pH was adjusted to 1.5 and 330 mg of sodium bisulfite was added. The pH was adjusted to 1.7 and stirring was continued. After 5 minutes, the layers were separated and the aqueous layer was further extracted with ethyl acetate. The combined ethyl acetate solutions were washed with brine, dried ($MgSO_4$) and evaporated in vacuo. This afforded 216 mg of the title compound as white crystals. The NMR spectrum (in $D_2O$) showed absorptions at 5.78 (d, 1H, J=4 Hz), 5.25 (d, 1H, J=4 Hz), 4.20 (s, 1H), 1.65 (s, 3H) and 1.46 (s, 3H) ppm. The IR spectrum (KBr disc) showed an absorption at 1790 $cm^{-1}$.

The latter product was suspended in ethyl acetate, and then a small volume of water, followed by 57 mg of sodium bicarbonate, was added. This mixture was stirred for 15 minutes, and then the aqueous phase was removed and lyophilized. This afforded 140 mg of the sodium salt of the title compound. The NMR spectrum (in $D_2O$) showed absorptions at 5.80 (d, J=4 Hz, 1H), 5.25 (d, J=4 Hz, 1H), 4.30 (s, 1H), 1.55 (s, 3H) and 1.45 (s, 3H). The IR spectrum (KBr disc) showed an absorption at 1790 $cm^{-1}$.

EXAMPLE 5

6-beta-Iodopenicillanic Acid 1,1-Dioxide

Oxidation of 6-beta-iodopenicillanic acid with potassium permanganate, according to the procedure of Example 4, affords 6-beta-iodopenicillanic acid, 1,1-dioxide.

EXAMPLE 6

Pivaloyloxymethyl 6-alpha-Bromopenicillanate 1,1-Dioxide

To a solution of 394 mg of pivaloyloxymethyl 6-alpha-bromopenicillanate in 10 ml of dichloromethane is added 400 mg of 3-chloroperbenzoic acid at 0° to 5° C. The reaction mixture is stirred at 0° to 5° C. for 1 hour and then at 25° C. for 24 hours. The filtered reaction mixture is evaporated to dryness in vacuo to give the title compound.

EXAMPLE 7

The procedure of Example 6 is repeated, except that the pivaloyloxymethyl 6-alpha-bromopenicillanate is replaced by:
3-phthalidyl 6-alpha-chloropenicillanate,
4-crotonolactonyl 6-beta-chloropenicillanate,
gamma-butyrolacton-4-yl 6-alpha-bromopenicillanate,
acetoxymethyl 6-beta-bromopenicillanate,
pivaloyloxymethyl 6-beta-bromopenicillanate,
hexanoyloxymethyl 6-alpha-iodopenicillanate,
1-(acetoxy)ethyl 6-beta-iodopenicillanate,
1-(isobutyryloxy)ethyl 6-alpha-chloropenicillanate,
1-methyl-1-(acetoxy)ethyl 6-beta-chloropenicillanate,
1-methyl-1-(hexanoyloxy)ethyl 6-alpha-bromopenicillanate,
methoxycarbonyloxymethyl 6-alpha-bromopenicillanate,
propoxycarbonyloxymethyl 6-beta-bromopenicillanate,
1-(ethoxycarbonyloxy)ethyl 6-alpha-bromopenicillanate,
1-(butoxycarbonyloxy)ethyl 6-alpha-iodopenicillanate,
1-methyl-1-(methoxycarbonyloxy)ethyl 6-beta-iodopenicillanate and
1-methyl-1-(isopropoxycarbonyloxy)ethyl 6-alpha-chloropenicillanate,
respectively. This affords:
3-phthalidyl 6-alpha-chloropenicillanate 1,1-dioxide,
4-crotonolactonyl 6-beta-chloropenicillanate 1,1-dioxide,
gamma-butyrolacton-4-yl 6-alpha-bromopenicillanate 1,1-dioxide,
acetoxymethyl 6-beta-bromopenicillanate 1,1-dioxide,
pivaloyloxymethyl 6-beta-bromopenicillanate 1,1-dioxide,
hexanoyloxymethyl 6-alpha-iodopenicillanate 1,1-dioxide,
1-(acetoxy)ethyl 6-beta-iodopenicillanate 1,1-dioxide,
1-(isobutyryloxy)ethyl 6-alpha-chloropenicillanate 1,1-dioxide,
1-methyl-1-(acetoxy)ethyl 6-beta-chloropenicillanate 1,1-dioxide,
1-methyl-1-(hexanoyloxy)ethyl 6-alpha-bromopenicillanate 1,1-dioxide,
methoxycarbonyloxymethyl 6-alpha-bromopenicillanate 1,1-dioxide,
propoxycarbonyloxymethyl 6-beta-bromopenicillanate 1,1-dioxide,
1-(ethoxycarbonyloxy)ethyl 6-alpha-bromopenicillanate 1,1-dioxide,
1-(butoxycarbonyloxy)ethyl 6-alpha-iodopenicillanate 1,1-dioxide,
1-methyl-1-(methoxycarbonyloxy)ethyl 6-beta-iodopenicillanate 1,1-dioxide and
1-methyl-1-(isopropoxycarbonyloxy)ethyl 6-alpha-chloropenicillanate 1,1-dioxide,
respectively.

EXAMPLE 8

Penicillanic Acid 1,1-Dioxide

To 100 ml of water was added 9.4 g of 6-alpha-bromopenicillanic acid, 1,1-dioxide, at 22° C., followed by sufficient 4 N sodium hydroxide solution to achieve a stable pH of 7.3. To the resulting solution was added 2.25 g of 5% palladium-on-carbon followed by 6.9 g of dipotassium phosphate trihydrate. This mixture was then shaken under an atmosphere of hydrogen at a pressure varying from 3.5 to 1.8 $kg/cm^2$. When hydrogen uptake ceased, the solids were removed by filtration, and the aqueous solution was covered with 100 ml of ethyl acetate. The pH was slowly lowered from 5.0 to 1.5 with 6 N hydrochloric acid. The layers were separated, and the aqueous phase was extracted with further ethyl acetate. The combined ethyl acetate layers were washed with brine, dried using anhydrous magnesium sulfate and evaporated in vacuo. The residue was triturated under ether and then the solid material was collected by filtration. This afforded 4.5 g (65% yield) of the title compound.

Analysis: Calcd. for $C_8H_{11}NO_5S$: C, 41.20; H, 4.75; N, 6.00; S, 13.75%. Found: C, 41.16, H, 4.81; N, 6.11; S, 13.51%.

EXAMPLE 9

Penicillanic Acid 1,1-Dioxide

Hydrogenolysis of each of:
6-alpha-chloropenicillanic acid 1,1-dioxide,
6-alpha-iodopenicillanic acid 1,1-dioxide,
6-beta-chloropenicillanic acid 1,1-dioxide,
6-beta-bromopenicillanic acid 1,1-dioxide and
6-beta-iodopenicillanic acid 1,1-dioxide,
according to the procedure of Example 8, affords penicillanic acid 1,1-dioxide.

EXAMPLE 10

Pivaloyloxymethyl Penicillanate 1,1-Dioxide

To a solution of 1.0 g of pivaloyloxymethyl 6-alpha-bromopenicillanate in 10 ml of methanol is added 3 ml of 1 M sodium bicarbonate and 200 mg of 10% palladium on carbon. The reaction mixture is shaken vigorously under an atmosphere of hydrogen, at a pressure of about 5 $kg/cm^2$, until hydrogen uptake ceases. The mixture is then filtered and the bulk of the methanol is removed by evaporation in vacuo. Water and ethyl acetate are added to the residue and the pH is adjusted to 8.5. The layers are separated and the organic layer is washed with water, dried ($Na_2SO_4$) and evaporated in vacuo. This affords the title compound.

EXAMPLE 11

Hydrogenolysis of the appropriate 6-halopenicillanic acid ester 1,1-dioxide from Example 7, according to the procedure of Example 10, affords the following compounds:

3-phthalidyl penicillanate 1,1-dioxide, 4-crotonolactonyl penicillanate 1,1-dioxide, gamma-butyrolacton-4-yl penicillanate 1,1-dioxide, acetoxymethyl penicillanate 1,1-dioxide, pivaloyloxymethyl penicillanate, 1,1-dioxide, hexanoyloxymethyl penicillanate, 1,1-dioxide, 1-(acetoxy)ethyl penicillanate 1,1-dioxide, 1-(isobutyryloxy)ethyl penicillanate 1,1-dioxide, 1-methyl-1-(acetoxy)ethyl penicillanate, 1,1-dioxide, 1-methyl-1-(hexanoyloxy)ethyl penicillanate 1,1-dioxide, methoxycarbonyloxymethyl penicillanate 1,1-dioxide, propoxycarbonyloxymethyl penicillanate, 1,1-dioxide, 1-(ethoxycarbonyloxy)ethyl penicillanate 1,1-dioxide, 1-(butoxycarbonyl)ethyl penicillanate 1,1-dioxide, 1-methyl-1-(methoxycarbonyloxy)ethyl penicillanate 1,1-dioxide and 1-methyl-1-(isopropoxycarbonyloxy)ethyl penicillanate 1,1-dioxide, respectively.

EXAMPLE 12

6-alpha-Chloropenicillanic Acid 1,1-Dioxide

The title compound was prepared by oxidation of 6-alpha-chloropenicillanic acid using potassium permanganate, substantially according to the procedure of Example 1. A portion (1.4 g.) was dissolved in a small volume of aqueous tetrahydrofuran and the pH was adjusted to a constant 7.0 with sodium hydroxide solution. The tetrahydrofuran was removed by evaporation in vacuo, and the aqueous residue was lyophilized to give the sodium salt of the title compound. The IR spectrum (nujol) showed absorptions at 1780 and 1605 $cm^{-1}$. The NMR spectrum ($D_2O$) showed absorptions at 5.40 (d, 1H, J=2 Hz), 5.20 (d, 1H, J=2 Hz), 4.35 (s, 1H), 1.60 (s, 3H) and 1.45 (s, 3H) ppm.

PREPARATION A

6-Chloro-6-iodopenicillanic Acid

To 3.38 g. of iodine monochloride in 30 ml. of dichloromethane was added, with stirring, at 0°–5° C., 11.1 ml. of 2.5 N sulfuric acid, followed by 1.92 g. of sodium nitrite. At this point, 3.00 g. of 6-aminopenicillanic acid was added all at once, and stirring was continued for 30 minutes at 0°–5° C. To the reaction mixture was then added 22.8 ml. of 1 M sodium sulfite solution in portions, and the layers were separated. The aqueous layer was washed with further dichloromethane, and then all the organic phases were washed with saturated sodium chloride. The dichloromethane solution was dried ($Na_2SO_4$) and evaporated in vacuo giving 3.48 g. of the title compound.

The above product was dissolved in 30 ml. of tetrahydrofuran, and then 30 ml. of water were added. The pH was adjusted to 6.8 with dilute sodium hydroxide and the tetrahydrofuran was removed in vacuo. The remaining aqueous phase was freeze-dried and the residue was washed with diethyl ether. This afforded 3.67 g. of the title compound as its sodium salt.

PREPARATION B 6-beta-Chloropenicillanic Acid

A 2.95-g. sample of sodium 6-chloro-6-iodopenicillanic acid was converted to the free acid, and then it was dissolved in 125 ml. of benzene under nitrogen. To the solution was added 1.08 ml. of triethylamine, and the mixture was cooled to 0°–5° C. To the cooled mixture was then added 0.977 ml. of trimethylsilyl chloride, and the reaction mixture was stirred at 0°–5° C. for 5 minutes, at 25° C. for 60 minutes and at 50° C. for 30 minutes. The reaction mixture was cooled to 25° C. and the triethylamine hydrochloride was removed by filtration. To the filtrate was added 15 mg. of azobisisobutyronitrile, followed by 2.02 ml. of tri-n-butyltin hydride. The mixture was then irradiated with ultraviolet light for 15 minutes with cooling to maintain at temperature of ca. 20° C. The solvent was then removed by evaporation in vacuo, and the residue was dissolved in a 1:1 mixture of tetrahydrofuran-water. The pH was adjusted to 7.0 and the tetrahydrofuran was removed by evaporation in vacuo. The aqueous phase was washed with ether, and then an equal volume of ethyl acetate was added. The pH was adjusted to 1.8 and the ethyl acetate layer was removed. The aqueous phase was extracted with further ethyl acetate, and then the combined ethyl acetate solutions were dried and evaporated in vacuo. This afforded 980 mg. of 6-beta-chloropenicillanic acid.

The above product was dissolved in tetrahydrofuran, and an equal volume of water was added. The pH was adjusted to 6.8, and the tetrahydrofuran was removed by evaporation in vacuo. The aqueous phase remaining was freeze-dried to give 850 mg. of sodium 6-beta-chloropenicillanate. The NMR spectrum ($D_2O$) showed absorption at 5.70 (d, 1H, J=4 Hz), 5.50 (d, 1H, J=4 Hz), 4.36 (s, 1H), 1.60 (s, 3H) and 1.53 (s, 3H) ppm.

PREPARATION C 6-beta-Bromopenicillanic Acid

A mixture of 5.0 g. of 6,6-dibromopenicillanic acid, 1.54 ml. of triethylamine and 100 ml. of benzene was stirred under nitrogen until a solution was obtained. The solution was cooled to 0°–5° C., and 1.78 ml. of trimethylsilyl chloride was added. The reaction mixture was stirred at 0°–5° C. for 2–3 minutes, and then at 50° C. for 35 minutes. The cooled reaction mixture was filtered and the filtrate was cooled to 0°–5° C. A small quantity of azobisisobutyronitrile was added followed by 3.68 ml. of tri-n-butyltin hydride. The reaction flask was irradiated with ultraviolet light for 15 minutes, and then the reaction was stirred at ca. 25° C. for 1.75 hours. The reaction mixture was irradiated again for 15 minutes and then stirring was continued 2.5 hours. At this point a further small quantity of azobisisobutyronitrile was added, followed by 0.6 ml. of tri-n-butyltin hydride (0.6 ml.), added and the mixture was again irradiated for 30 minutes. The solvent was then removed by evaporation in vacuo, and to the residue was added 5% sodium bicarbonate solution and diethyl ether. The two-phase system was shaken vigorously for 10 minutes and then the pH was adjusted to 2.0. The ether layer was removed, dried and evaporated in vacuo to give 2.33 g. of an oil. The oil was converted into a sodium salt by adding water containing 1 equivalent of sodium bicarbonate followed by freeze drying the solution thus obtained. The afforded sodium 6-beta-bromopenicillanate, contaminated with a small amount of the alpha-isomer.

The sodium salt was purified by chromatography on Sephadex LH-20, combined with some further material of the same quality and re-chromatographed. The NMR spectrum (D$_2$O) of the product thus obtained showed absorptions at 5.56 (s, 2H), 4.25 (s, 1H), 1.60 (s, 3H) and 1.50 (s, 3H) ppm.

PREPARATION D

6-beta-Iodopenicillanic Acid

The title compound is prepared by reduction of 6,6-diiodopenicillanic acid, with tri-n-butyltin hydride, according to the procedure of Preparation B.

PREPARATION E

Pivaloyloxymethyl 6-alpha-Bromopenicillanate

To a solution of 280 mg. of 6-alpha-bromopenicillanic acid in 2 ml. of N,N-dimethylformamide is added 260 mg. of diisopropylethylamine followed by 155 mg. of chloromethyl pivalate and 15 mg. of sodium iodide. The reaction mixture is stirred at room temperature for 24 hours, and then it is diluted with ethyl acetate and water. The pH is adjusted to 7.5, and then the ethyl acetate layer is separated and washed three times with water and once with saturated sodium chloride solution. The ethyl acetate solution is then dried using anhydrous sodium sulfate, and evaporated in vacuo to give the title compound.

PREPARATION F

Reaction of the appropriate 6-halopenicillanic acid with 3-phthalidyl chloride, 4-crotonolactonyl chloride, gamma-butyrolacton-4-yl chloride or the requisite alkanoyloxymethyl chloride, 1-(alkanoyloxy)ethyl chloride, 1-methyl-1-(alkanoyloxy)ethyl chloride, alkoxycarbonyloxymethyl chloride, 1-(alkoxycarbonyloxy)ethyl chloride or 1-methyl-1-(alkoxycarbonyloxy)ethyl chloride, according to the procedure of Preparation E, affords the following compounds:
3-phthalidyl 6-alpha-chloropenicillanate,
4-crotonolactonyl 6-beta-chloropenicillanate,
gamma-butyrolacton-4-yl 6-alpha-bromopenicillanate,
acetoxymethyl 6-beta-bromopenicillanate,
pivaloyloxymethyl 6-beta-bromopenicillanate,
hexanoyloxymethyl 6-alpha-iodopenicillanate,
1-(acetoxy)ethyl 6-beta-iodopenicillanate,
1-(isobutyryloxy)ethyl 6-alpha-chloropenicillanate,
1-methyl-1-(acetoxy)ethyl 6-beta-chloropenicillanate,
1-methyl-1-(hexanoyloxy)ethyl 6-alpha-bromopenicillanate,
methoxycarbonyloxymethyl 6-alpha-bromopenicillanate,
propoxycarbonyloxymethyl 6-beta-bromopenicillanate,
1-(ethoxycarbonyloxy)ethyl 6-alpha-bromopenicillanate,
1-butoxycarbonyloxy)ethyl 6-alpha-iodopenicillanate,
1-methyl-1-(methoxycarbonyloxy)ethyl 6-beta-iodopenicillanate, and
1-methyl-1-(isopropoxycarbonyloxy)ethyl 6-alpha-chloropenicillanates,
respectively.

PREPARATION G

6,6-Diiodopenicillanic Acid

A mixture of 15.23 g. of iodine, 10 ml. of 2.5 N sulfuric acid, 2.76 g. of sodium nitrite and 75 ml. of dichloromethane was stirred at 5° C., and 4.32 g. of 6-aminopenicillanic acid were added over a period of 15 minutes. Stirring was continued at 5°–10° C. for 45 minutes after the addition was complete, and then 100 ml. of 10% sodium bisulfite was added dropwise. The layers were separated, and the aqueous layer was further extracted with dichloromethane. The combined dichloromethane layers were washed with brine, dried (MgSO$_4$) and evaporated in vacuo. This afforded 1.4 g. of the title compound, contaminated with some 6-iodopenicillanic acid. The product had a melting point of 58°–64° C. The NMR spectrum (CDCl$_3$) showed absorptions at 5.77 (s, 1H), 4.60 (s, 1H), 1.71 (s, 3H) and 1.54 (s, 3H) ppm.

PREPARATION H

Sodium 6-beta-Bromopenicillanate

To a stirred solution of 1.83 g of 6,6-dibromopenicillanic acid and 0.7 ml of triethylamine in 4.6 ml of toluene was added 0.64 ml of trimethylsilyl chloride, at 20° C., under nitrogen. Stirring was continued at 20° C. for 30 minutes, and then the precipitate was removed by filtration. To the filtrate was added, dropwise, under nitrogen, at 20° C., 1.3 ml of triphenyltin hydride in 1 ml of toluene, during 10 minutes. Stirring was continued at 20° C. for 5 hours, and then the reaction mixture was filtered, and stirring was continued a further 1 hour at 20° C. At this point 100 ml of sodium bicarbonate solution was added and the aqueous phase was removed. Ethyl acetate was added to the aqueous phase and the biphasic mixture was cooled to 0°–5° C. The pH was lowered to 1.5 with 6 N hydrochloric acid and the ethyl acetate layer was removed. The latter solution was dried with magnesium sulfate and then 4.2 ml (1.24 mmol/ml) of sodium 2-ethylhexanoate in ethyl acetate was added. The resulting mixture was stored at ca. 5° C. overnight and then it was concentrated to 5 ml volume. The solid was recovered by filtration and washed with acetone to give 380 mg of the title compound, contaminated with about 13% of penicillanic acid sodium salt.

PREPARATION I

Sodium 6-beta-Iodopenicillanate

To a stirred solution of 4.0 g of 6,6-diiodopenicillanic acid in 16 ml of toluene and 10 ml of tetrahydrofuran, under nitrogen was added 1.24 ml of triethylamine followed by 1.146 ml of trimethylsilyl chloride. Stirring was continued for 30 minutes and the precipitate was removed by filtration. To the filtrate was added a solution of 2.09 ml of tri-n-butyltin hydride in 3.1 ml of toluene. After 30 minutes of stirring, 22.38 ml of water was added, and the layers were separated. The organic layer was washed with saturated sodium chloride solution, dried using magnesium sulfate, and then it was concentrated to about two-thirds volume. To this solution was then added a solution containing 8.77 mmole of sodium 2-ethylhexanoate in 7 ml of toluene, at 0° to 5° C., with stirring. Stirring was continued for 1.5 hours at 0° to 5° C. The precipitate which had formed was removed by filtration, and slurried in hexane. The solid was recovered by filtration to give 0.921 g of product, which was a 1:1 mixture of the title compound and its 6-alpha isomer. The two components can be separated by chromatography on sephadex or silica gel.

PREPARATION J

6-Beta-Iodopenicillanic Acid Pivaloyloxymethyl Ester

A. 6,6-diiodopenicillanic acid pivaloyloxy methyl ester

A mixture of 5.94 g. of sodium nitrite in 260 ml. of water and 2.63 g. of 6-beta-aminopenicillanic acid pivaloyloxymethyl ester in 260 ml. of methylene chloride was stirred with cooling in an ice bath. p-Toluenesulfonic acid (1.2 g.) was added in three portions over a period of 30 minutes and the mixture was allowed to stir for one hour at room temperature. The organic phase was separated and dried over sodium sulfate. Iodine (1.3 g.) was added to the organic phase and the resulting solution allowed to stir at room temperature for 4 hours. The solution was washed with aqueous sodium thiosulfate, separated and concentrated in vacuo to a low volume. The residue was chromatographed on silica gel using petroleum ether (b.p. 60°–80°) containing an increasing proportion of ethyl acetate as the eluent. The fractions containing the product were combined, dried over sodium sulfate and concentrated under vacuum to dryness to give 1.43 g., m.p. 136°–138° C. The NMR spectrum (CDCl$_3$) showed absorption at 5.79 (bs, 2H), 5.71 (s, 1H), 4.52 (s, 1H), 1.65 (s, 3H), 1.44 (s, 3H) and 1.21 (s, 9H) ppm.

B. 6-beta-iodopenicillanic acid pivaloyloxymethyl ester

To a solution of 1.29 g. of 6,6-diiodopenicillanic acid pivaloyloxymethyl ester in 8 ml. of benzene under a nitrogen atmosphere was added 500 mg. of triphenyltin hydride and a few crystals (10 mg.) of azobisisobutyronitrile, and resulting reaction mixture was warmed to 50° C. for one hour. An additional 500 mg. of hydride and 10 mg. of nitrile were added and the heating continued with stirring for 3 hours. Column chromatographing on silica gel using petroleum ether (b.p. 60°–80° C.) with an increasing proportion of methylene chloride as the eluent gave 140 mg. of the desired product, m.p. 73°–77° C. The NMR spectrum (CDCl$_3$) showed absorption at 5.9 (d, AB, J=5.8 Hz), 5.82 (d, AB, J=5.8 Hz), 5.66 (d, 1H, AB, J=4.1 Hz), 5.42 (d, 1H, AB, J=4.1 Hz), 4.59 (s, 1H), 1.71 (s, 3H), 1.50 (s, 3H) and 1.24 (s,9H) ppm.

PREPARATION K

6-Beta-Iodopenicillanic Acid

A. 6,6-diiodopenicillanic acid benzhydryl ester

To a solution of 5.94 g. of sodium nitrite in 250 ml. of water at 5° C. was added with stirring 2.9 g. of 6-beta-aminopenicillanic acid benzhydryl ester tosylate salt in 250 ml. of methylene chloride. p-Toluene sulfonic acid (1.2 g.) was added in three portions over a period of 30 minutes and the mixture allowed to stir for one hour at room temperature. The organic phase was separated, dried over sodium sulfate and treated with 1.3 g. of iodine. The resulting solution was stirred at room temperature for 4 hours and was then washed with an aqueous sodium thiosulfate solution and concentrated to a low volume. The residue was chromatographed on silica gel using petroleum ether with increasing proportions of ethyl acetate as the eluent. The fraction containing the product were combined and concentrated in vacuo to give the desired product.

B. 6-beta-iodopenicillanic acid benzhydryl ester

To a solution of 1.92 g. of 6,6-diiodopenicillanic acid benzhydryl ester in 8 ml. of benzene was added 500 mg. of triphenyltin hydride and 10 mg. of azobisisobutyronitrile, and the resulting reaction mixture allowed to stir under a nitrogen atmosphere at 50° C. for one hour. An additional amount of hydride (500 mg.) and nitrile (10 mg.) was added and heating at 50° C. continued for 3 hours. The solvent was removed under vacuum and the residue chromatographed over silica gel using petroleum ether with increasing proportions of ethyl acetate as the eluent. The fractions containing the product were combined and concentrated to dryness. The NMR spectrum (CDCl$_3$) showed absorption at 7.50 (bs, 10H), 6.97 (s, 1H), 5.66 (d, 1H, AB, J=4.0 Hz), 5.44 (d, 1H, AB, J=4.0 Hz), 4.67 (s, 1H), 1.70 (s, 3H) and 1.40 (s, 3H) ppm.

C. 6-beta-iodopenicillanic acid

Trifluoroacetic acid (0.5 ml.) was added to 80 mg. of 6-beta-iodopenicillanic acid benzhydryl ester in 1 ml. of methylene chloride and the reaction mixture stirred for 30 minutes at room temperature. The mixture was evaporated to dryness to yield 76 mg. of crude product. Purification is effected by chromatography on silica gel.

PREPARATION L

6-Beta-Iodopenicillanic Acid

A. 6,6-diiodopenicillanic acid 4-methoxybenzyl ester

The title compound was prepared from 6-beta-aminopenicillanic acid 4-methoxybenzyl ester following the procedure of Preparation K (Part A).

B. 6-beta-iodopenicillanic acid 4-methoxybenzyl ester

The title compound was prepared from 6,6-diiodopenicillanic acid 4-methoxybenzyl ester using the procedure of Preparation K (Part B). The NMR (CDCl$_3$) spectrum shows absorption at 7.36 (d, 2H, AA', XX', J=9 Hz), 6.95 (d, 2H, AA', XX', J=9.0 Hz), 5.65 (d, 1H, AB, J=4.2 Hz), 5.42 (d, 1H, AB, J=4.2 Hz), 4.58 (s, 1H), 3.89 (s, 3H), 1.71 (s, 3H), 1.70 (s, 3H) and 1.39 (s, 3H) ppm.

C. 6-beta-iodopenicillanic acid

6-Beta-iodopenicillanic acid 4-methoxybenzyl ester (90 mg.) was dissolved in 2 ml. of methylene chloride to which was then added 1 ml. of trifluoroacetic acid and 3 drops of anisole. The mixture was stirred at room temperature for 5 hours and was then evaporated to dryness. The residue was chromatographed on silica using petroleum ether and then ethyl acetate as the eluent. The fractions containing the product were combined and concentrated to give 40 mg. of the desired product. The NMR (CDCl$_3$) spectrum showed absorption ca. 9 (bs, 1H), 5.65 (d, 1H, AB, J4.0 Hz), 5.39 (d, 1H, AB, J=4.0 Hz), 4.57 (s, 2H), 1.74 (s, 3H) and 1.57 (s, 3H).

PREPARATION M

Preparation of Benzhydryl 6-alpha-Trifluoromethanesulfonyloxypenicillanate

Sodium nitrite (55 g, 0.80 mole) was added to a cold stirred solution of p-toluenesulfonic acid monohydrate (12.5 g, 0.065 moles) in a mixture of water (1.25 l) and methylene chloride (1.25 l) and the mixture was stirred at 5° C. for 15 minutes. Benzhydryl 6-beta-aminopenicillanate p-toluenesulfonate salt (27.75 g, 0.05 mole) was added and the mixture stirred vigorously at 5°–7° C. for 30 minutes. The organic layer was separated, dried over anhydrous magnesium sulfate and filtered. Powdered magnesium silicate (8 g) was added and the filtrate cooled to 5° C. and stirred while trifluoromethanesulfonic acid (8.0 g, 0.055 mole) was added dropwise over 15 minutes keeping the temperature below 10° C. The addition was accompanied by vigorous evolution of nitrogen. After stirring for a further 15 minutes the solution was filtered and the filtrate was evaporated to dryness under vacuum at 40° C. to yield the product as a tan foam (22 g, 92%).

N.M.R. ($CD_3COCD_3$) delta: 1.35 (s, 3H), 1.60 (s,3H); 4.82 (s, 1H), 5.72 (d, 1H, J=1.5 Hz); 5.90 (s, 1H), 6.95 (s, 1H), 7.3 (m, 10H).

T.L.C. (silica/ethyl acetate): Rf 0.8.

A small sample was recrystallized from hexane and had m.p. 44°-45° C. (dec.).

PREPARATION N 6-alpha-Trifluoromethylsulfonyloxypenicillanic Acid

4-Methoxybenzyl 6-alpha-trifluoromethylsulfonyloxypenicillanate (100 mg.) was dissolved in trifluoroacetic acid (1 ml.) and after 15 seconds evaporated to dryness. Column chromatography of the residue on silica eluting with petrol containing increasing amounts of ethyl acetate yielded 62 mg. impure product, which was triturated with diisopropyl ether and purified by preparative t.l.c. on silica with 5% acetic acid in ethyl acetate to give pure 6-alpha-trifluoromethylsulfonyloxypenicillanic acid (17 mg.).

T.L.C.: $R_f$ 0.45 (5% acetic acid/ethyl acetate on $SiO_2$).

N.M.R. ($CDCl_3$) delta: 1.57 (s, 3H); 1.61 (s, 3H); 4.56 (s, 1H); 5.51 (s, 2H); 9.07 (bs, HO group).

I.R. (film): 1815 $cm^{-1}$ (beta-lactam carbonyl).

PREPARATION O 6-alpha-Trifluoromethylsulfonyloxypenicillanic Acid 4-methoxybenzyl ester A solution of trifluoromethane sulfonyl chloride (0.70 g.) in chloroform (2 ml.) was added dropwise to a stirred ice-cold solution of 6-alpha-hydroxypenicillanic acid 4-methoxybenzyl ester (0.93 g.) and triethylamine (0.55 g.) in chloroform (50 ml.). After 15 minutes the solution was washed with water (50 ml.), dried ($MgSO_4$) and evaporated to dryness. The product was chromatographed on silica eluting with pentane containing an increasing proportion of dichloromethane.

Evaporation of the relevant fractions gave 6-alpha-trifluoromethylsulfonyloxypenicillanic acid 4-methoxybenzyl ester (0.70 g.), m.p. 69°-71° C.

Analysis %: Found: C, 43.59; H, 3.81; N, 2.62. $C_{17}H_{18}NO_7SF_3$ requires: C, 43.50; H, 3.84; N, 2.99.

N.M.R. ($CDCl_3$) delta: 1.36 (s, 3H); 1.53 (s, 3H); 3.80 (s, 3H); 4.52 (s, 1H); 5.12 (s, 2H); 5.48 (2H); 7.08 (q, 4H).

T.L.C. (silica/dichloromethane): $R_f$ 0.3.

PREPARATION P 6-beta-Iodopenicillanic Acid (A) A mixture of 6-alpha-trifluorosulfonyloxypenicillanic acid 4-methoxybenzyl ester (5 g.), sodium iodide (12.5 g.) and acetone (100 ml.) was stirred at room temperature for 46 hours. The resulting mixture was concentrated to 10 ml., diluted with water (200 ml.) and extracted with ether (200 ml.). The ether extract was dried over $MgSO_4$ and evaporated to yield 6-beta-iodopenicillanic acid 4-methoxybenzyl ester as an oil (4.8 g.).

(B) Trifluoroacetic acid (2 ml.) was added to a solution of the product from A (0.38 g.) in dichloromethane (20 ml.). The solution was stirred at room temperature for 30 minutes and the solution was then evaporated under vacuum and the residue chromatographed on a column of silica eluting with a 1:3 mixture of ethyl acetate and petroleum ether (b.p. 60°-80° C.). The relevant fractions containing the product were combined and evaporated to a low volume. The crystalline precipitate was collected by filtration, washed with a 1:1 mixture of dichloromethane and pentane and dried to yield 6-beta-iodopenicillanic acid (27 mg.), m.p. 120° C. (dec.).

The product was spectroscopically and chromatographically identical to a reference sample.

N.M.R. ($CDCl_3$) delta: 1.57 (s, 3H); 1.74 (s, 3H); 4.57 (s, 1H+1H); 5.39 (d, 1H, J=4.0 Hz); 5.65 (d, 1H, J=4.0 Hz); 9.0 (bs, 1H).

PREPARATION Q 6-beta-Iodopenicillanic Acid (A) The procedure of Preparation O, Part A, was followed using 6-alpha-trifluoromethylsulfonyloxypenicillanic acid benzhydryl ester to give 6-beta-iodopenicillanic acid benzhydryl ester.

N.M.R. ($CDCl_3$) delta: 1.24 (s, 3H); 1.65 (s, 3H); 4.62 (s, 1H); 5.36 (d, 1H); 5.56 (d, 1H); 6.95 (s, 1H); 7.36 (s, 10H).

(B) 6-beta-Iodopenicillanic acid benzhydryl ester (80 mg.) was dissolved in dichloromethane (1 ml.) and trifluoroacetic acid (0.5 ml.) added. The solution was stirred at room temperature for 30 minutes and then evaporated to dryness to yield 76 mg. of product, identified by thin-layer chromatography, i.r. spectrum and n.m.r. to be 6-beta-iodopenicillanic acid contaminated with some benzhydryl-derived by-product.

PREPARATION R

Sodium 6-beta-Iodopenicillanate (A) Bis(trimethylsilyl)acetamide (3.19 g., 157 mmoles) was added to a solution of 6-alpha-trifluoromethylsulfonyloxypenicillanic acid (5 g., 143 mmoles) in acetone (50 ml.) and the solution was stirred at 35°-40° C. for 30 minutes. Sodium iodide (2.35 g., 157 mmoles) was added to the resulting solution of 6-alpha-trifluoromethylsulfonyloxypenicillanic acid trimethylsilyl ester and the mixture was stirred at 60°-65° C. for 30 minutes. The solvent was evaporated under vacuum to yield 6-beta-iodopenicillanic acid trimethylsilyl ester as a thick red oil.

(B) The product from (A) was stirred with ethyl acetate (50 ml.) and water (50 ml.), the organic layer was separated, washed with water (2×25 ml.) and dried over anhydrous magnesium sulfate. A solution of sodium 2-ethylhexanoate (3.57 g., 215 mmoles) was added to the acetone solution of the acid and the mixture stirred at room temperature for 30 minutes.

The crystalline precipitate was collected by filtration, washed with ethyl acetate and ether and dried to yield sodium 6-beta-iodopenicillanate (3.3 g., 66%) identical to a reference sample.

PREPARATION S

6-alpha-Hydroxypenicillanic Acid 4-Methoxybenzyl Ester

Anisyl chloride (50.6 g.) was added to a stirred solution of 6-alpha-hydroxypenicillanic acid (71 g.) in N,N-dimethylformamide (540 ml.) containing triethylamine (57 g.). The mixture was stirred at room temperature for 17 hours and then partitioned between water (1 l.) and ethyl acetate (1 l.). The organic phase was separated, washed in turn with water (2×500 ml.), saturated sodium bicarbonate (500 ml.) and brine (500 ml.) and dried over magnesium sulfate. Evaporation of the solvent gave an oil which was chromatographed on silica eluting with petroleum ether (b.p. 60°–80° C.) to give 6-alpha-hydroxypenicillanic acid 4-methoxybenzyl ester (15 g., 13%) as an oil.

N.M.R. (CDCl$_3$) delta: 1.35 (s, 3H); 1.50 (s, 3H); 3.78 (s, 3H); 4.42 (s, 1H); 4.77 (d, 1H); 5.10 (s, 2H); 5.22 (d, 1H); 7.05 (q, 4H).

I claim:

1. (2S,5R,6S)-6-alpha-Bromo-3,3-dimethyl-7-oxo-4-thia-1-azabicyclo[3.2.0]heptane-2-carboxylic acid, S,S-dioxide, or a base salt thereof or a readily hydrolyzable ester thereof.

2. A compound in accordance with claim 1, (2S,5R,6S)-6-alpha-bromo-3,3-dimethyl-7-oxo-4-thia-1-azabicyclo[3.2.0]heptane-2-carboxylic acid, S,S-dioxide.

3. A compound of the formula

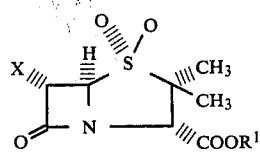

and the base salts thereof, wherein

R$^1$ is selected from the group consisting of hydrogen, alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gammabutyrolacton-4-yl; and X is selected from the group consisting of chloro, bromo and iodo.

4. A compound according to claim 3, wherein X is bromo.

5. The compound according to claim 4, wherein R$^1$ is hydrogen.

6. The compound according to claim 4, wherein R$^1$ is pivaloyloxymethyl.

7. The compound according to claim 4, wherein R$^1$ is 1-(ethoxycarbonyloxy)ethyl.

* * * * *